United States Patent
Yu et al.

(10) Patent No.: US 9,521,325 B2
(45) Date of Patent: Dec. 13, 2016

(54) TERMINAL DEVICE AND LINE OF SIGHT DETECTION METHOD

(71) Applicant: FUJITSU LIMITED, Kawasaki-shi, Kanagawa (JP)

(72) Inventors: Shanshan Yu, Kawasaki (JP); Satoshi Nakashima, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/284,937

(22) Filed: May 22, 2014

(65) Prior Publication Data

US 2014/0368687 A1 Dec. 18, 2014

(30) Foreign Application Priority Data

Jun. 14, 2013 (JP) ................................. 2013-125456

(51) Int. Cl.
*H04N 5/232* (2006.01)
*A61B 3/113* (2006.01)
*G06F 3/01* (2006.01)
*G06K 9/00* (2006.01)

(52) U.S. Cl.
CPC ........... *H04N 5/23248* (2013.01); *A61B 3/113* (2013.01); *G06F 3/013* (2013.01); *G06K 9/00604* (2013.01)

(58) Field of Classification Search
CPC . H04N 5/23248; G06K 9/00604; G06F 3/013; A61B 3/113
See application file for complete search history.

(56) References Cited

U.S. PATENT DOCUMENTS

| 5,410,376 A | 4/1995 | Cornsweet et al. |
| 7,460,150 B1 * | 12/2008 | Coughlan .............. H04N 7/147 348/14.01 |
| 8,204,312 B2 * | 6/2012 | Irie .................... G06K 9/00261 382/190 |
| 2007/0132663 A1 | 6/2007 | Iba et al. |
| 2007/0132874 A1 * | 6/2007 | Forman .............. H04N 5/23212 348/333.02 |
| 2010/0215283 A1 * | 8/2010 | Ono .............................. 382/255 |
| 2010/0328444 A1 * | 12/2010 | Blixt et al. ....................... 348/78 |

(Continued)

FOREIGN PATENT DOCUMENTS

| EP | 2 664 985 A2 | 11/2013 |
| JP | 2007-268164 | 10/2007 |

(Continued)

OTHER PUBLICATIONS

European Search Report issued Nov. 11, 2014 in corresponding European Patent Application No. 14170161.5.

*Primary Examiner* — Mekonnen Dagnew
(74) *Attorney, Agent, or Firm* — Staas & Halsey LLP

(57) ABSTRACT

A terminal device includes, a processor; and a memory which stores a plurality of instructions, which when executed by the processor, cause the processor to execute, obtaining information that indicates a state of an imaging unit when photographing a subject; determining whether an image photographed by the imaging unit includes blurriness due to shaking of the imaging unit based on the obtained information; and using an image determined as not including blurriness in the determining to detect a line of sight of the photographed subject.

10 Claims, 10 Drawing Sheets

(56) References Cited

U.S. PATENT DOCUMENTS

| | | | | |
|---|---|---|---|---|
| 2012/0206619 A1* | 8/2012 | Nitta | ................ | H04N 5/23219 |
| | | | | 348/222.1 |
| 2013/0141603 A1* | 6/2013 | Imada | ........................ | 348/208.6 |
| 2013/0155264 A1* | 6/2013 | Zhou | ................ | H04N 5/23258 |
| | | | | 348/208.6 |

FOREIGN PATENT DOCUMENTS

| | | |
|---|---|---|
| JP | 2011-90702 | 5/2011 |
| JP | 2011-192026 | 9/2011 |

* cited by examiner

TERMINAL DEVICE AND LINE OF SIGHT DETECTION METHOD

CROSS-REFERENCE TO RELATED APPLICATION

This application is based upon and claims the benefit of priority of the prior Japanese Patent Application No. 2013-125456, filed on Jun. 14, 2013, the entire contents of which are incorporated herein by reference.

FIELD

The embodiments discussed herein are relate to a terminal device that detects a line of sight of a human, a line of sight detection program, and a line of sight detection method.

BACKGROUND

Japanese Laid-open Patent Publication No. 2007-268164 and Japanese Laid-open Patent Publication No. 2011-90702, for example, discuss techniques for detecting the state of a person operating a computer or driving a vehicle based on detecting a line of sight of the person from an image photographed by a camera and using the motions of the detected line of sight. A camera used for detecting the line of sight in these techniques may be disposed in a fixed manner to the computer or the vehicle.

However, since a tablet terminal or a smartphone including a camera function is operated while being held by a person, the photographed image may be blurry due to camera shake and the like thus making the detection of the line of sight from the photographed image difficult. One aspect of the present disclosure is to detect the line of sight of a person with high precision.

SUMMARY

In accordance with an aspect of the embodiments, a terminal device includes, a processor; and a memory which stores a plurality of instructions, which when executed by the processor, cause the processor to execute, obtaining information that indicates a state of an imaging unit when photographing a subject; determining whether an image photographed by the imaging unit includes blurriness due to shaking of the imaging unit based on the obtained information; and using an image determined as not including blurriness in the determining to detect a line of sight of the photographed subject.

The object and advantages of the invention will be realized and attained by means of the elements and combinations particularly pointed out in the claims. It is to be understood that both the foregoing general description and the following detailed description are exemplary and explanatory and are not restrictive of the invention, as claimed.

BRIEF DESCRIPTION OF DRAWINGS

These and/or other aspects and advantages will become apparent and more readily appreciated from the following description of the embodiments, taken in conjunction with the accompanying drawing of which.

DESCRIPTION OF EMBODIMENTS

Hereinafter, embodiments will be discussed with reference to the drawings.

Figure 1:
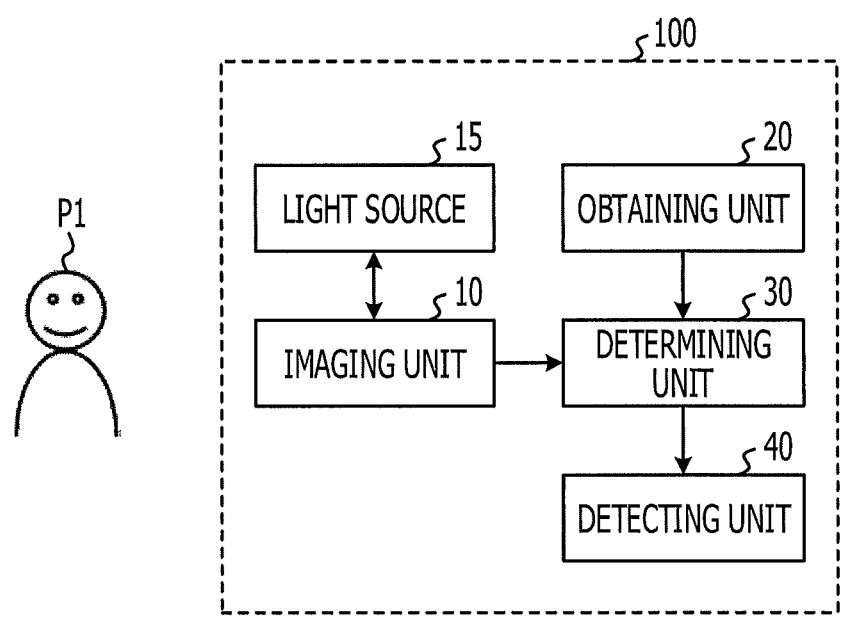
FIG. 1 illustrates a first embodiment of a terminal device.

FIG. 1 illustrates a first embodiment of a terminal device. A terminal device 100 illustrated in FIG. 1 is, for example, a smartphone or a tablet terminal and has an imaging unit 10, a light source 15, an obtaining unit 20, an determining unit 30, and a detecting unit 40. The terminal device 100 illustrated in FIG. 1 includes the light source 15, but may also omit the light source 15.

The imaging unit 10 is a camera that includes, for example, a lens and an imaging element such as a charge-coupled device (CCD) or a complementary metal-oxide semiconductor (CMOS). For example, the imaging unit 10 causes the light source 15, which is a light-emitting diode (LED) for emitting an infrared ray, to irradiate an infrared ray at a user P1 who is operating the hand-held terminal device 100. The imaging unit 10 generates an image by photographing the user P1 irradiated by the infrared ray. The imaging unit 10 outputs the generated image to the determining unit 30. The image generated by the imaging unit 10 is a still image or frames of a moving image. The user P1 is an example of a subject.

While the imaging unit 10 photographs the user P1 by causing the light source 15 to irradiate an infrared ray at the user P1, the user P1 may also be photographed without causing the light source 15 to irradiate an infrared ray. The imaging unit 10 is disposed in the terminal device 100 but is not limited thereto. For example, the imaging unit 10 may be disposed outside of the terminal device 100 in a fixed positional relationship with the terminal device 100. In this case, the imaging unit 10 is preferably connected to the terminal device 100 via a universal serial bus (USB) standard interface built into the terminal device 100 when photographing the user P1 operating the terminal device 100.

The obtaining unit 20 obtains information indicating a state of the imaging unit 10 when photographing the subject. For example, the obtaining unit 20 includes a gyro sensor and detects a parameter such as angular speed that indicates a change in the orientation of the terminal device 100. The obtaining unit 20 outputs the value of the detected parameter as information that indicates the state of the imaging unit 10 when photographing. While the obtaining unit 20 detects a parameter such as angular speed that indicates a change in the orientation of the terminal device 100, the obtaining unit 20 is not limited thereto. For example, the obtaining unit 20 may detect an angle of inclination indicating an orientation of the terminal device 100 and may output to the determining unit 30 a change amount of the angle of inclination before and after photographing as information indicating the state of the imaging unit 10 when photographing. Furthermore, the obtaining unit 20 may include an acceleration sensor and detect an acceleration of the terminal device 100 with the acceleration sensor, and may output to the determining unit 30 the acceleration as information indicating the state of the imaging unit 10 when photographing.

For example, the determining unit 30 determines whether the image photographed with the imaging unit 10 includes blurriness due to shaking of the imaging unit 10, based on the magnitude of the angular speed received from the obtaining unit 20. The determining unit 30 determines that the photographed image includes blurriness due to camera shake caused by the user P1 if, for example, the magnitude of the angular speed is equal to or greater than a threshold $\alpha$. The determining unit 30, for example, then discards the image determined as including blurriness. However, if the magnitude of the angular speed is less than the threshold $\alpha$, the determining unit 30 determines that the photographed image does not have blurriness and outputs the image to the detecting unit 40.

The threshold $\alpha$ is preferably set according to a magnitude of the angular speed that is determined by testing in the design stage or the manufacturing stage and the like, within a permissible range in which is obtained the precision of the line of sight detection expected for the detecting unit 40. Moreover, the magnitude of the angular speed obtained by the obtaining unit 20 may differ if the user P1 is operating the terminal device 100 while sitting in a chair and the like or if the user P1 is operating the terminal device 100 while on board a bus or a train and the like. Accordingly, the user P1 may appropriately set the threshold $\alpha$ in correspondence with an environment by using a keyboard or a touch panel provided on the terminal device 100 to select the operating environment of the terminal device 100.

The detecting unit 40 receives the image that is determined as not having blurriness by the determining unit 30, and detects the line of sight of the user P1. The operation of the detecting unit 40 is described with reference to FIG. 2.

Figure 2A:
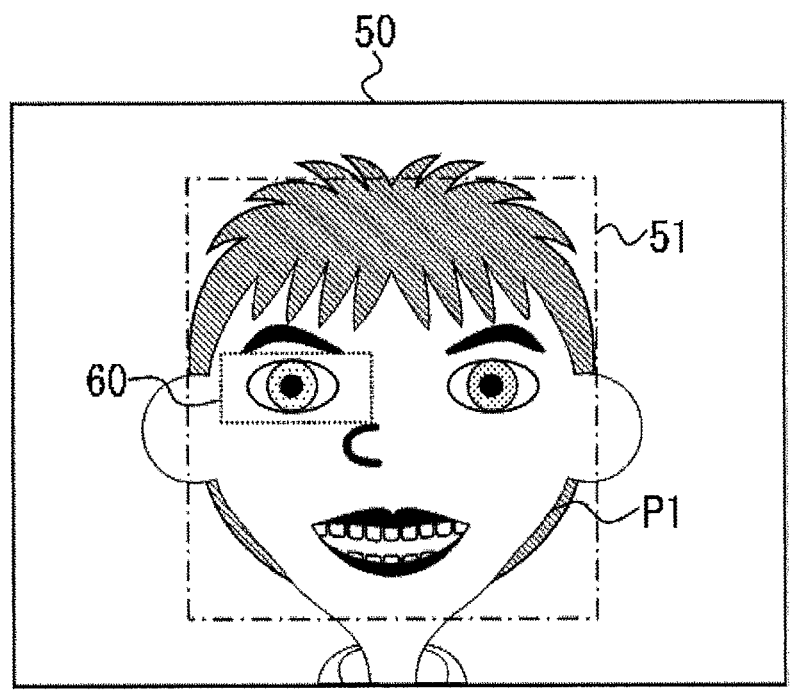
FIG. 2A is an example of an image generated by photographing by an imaging unit illustrated in FIG. 1.
Figure 2B:
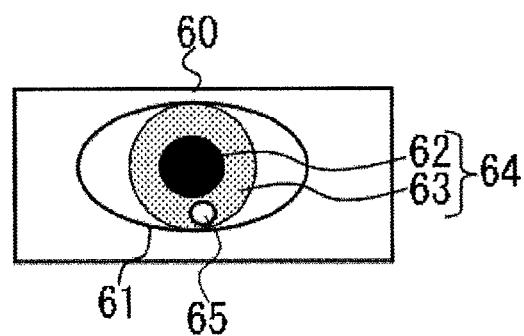
FIG. 2B is an example of an image generated by photographing by an imaging unit illustrated in FIG. 1.

FIG. 2 is an example of an image generated by photographing with the imaging unit 10 illustrated in FIG. 1. FIG. 2A is an example of an image 50 photographed with the imaging unit 10 with the user P1 operating the terminal device 100 as the subject. FIG. 2B is an example of a region 60 that includes an eye (e.g., the right eye) of the user P1 in the image 50 illustrated in FIG. 2A.

The detecting unit 40 detects a region 51, for example, including the face of the user P1 from the image 50 received from the determining unit 30 as illustrated in FIG. 2A. For example, the detecting unit 40 extracts characteristic points such as edges indicating a non-continuous change in brightness in the image 50, and specifies edge points of the eyebrows, the eyes, the nose, the lips and the like based on the dispersion of the extracted characteristic points. The detecting unit 40 then detects the region 51 based on the positions of the specified edge points. Alternatively, the detecting unit 40 may derive a correlation between a template of a face image and the received image 50 and may detect an image region for which the derived correlation coefficient is equal to or greater than a certain value. For example, the face image template may be stored beforehand in an electrically erasable programmable read-only memory (EEPROM) built into the terminal device 100.

The detecting unit 40 detects the region 60 that includes the eye and an eye contour 61 from the region 51 based on information such as the edge points of the eye specified during the extraction of the region 51. The detecting unit 40 then detects a region in the image region inside the detected contour 61 in which, for example, the characteristic points such as edges are dispersed in a circular shape and a brightness value of the circular region is lower than a brightness value of the surrounding regions, as a region 64 that includes a pupil 62 and an iris 63. The detecting unit 40 derives the center position of the pupil 62 from the detected region 64. The detecting unit further detects a light spot that indicates the position in which the infrared ray irradiated from the light source 15 is reflected by the cornea of the eye of the user P1, as a reflected image 65 of the light source 15 due to the cornea having a brightness value equal to or greater than a certain threshold and having a round shape in the region 64. The detecting unit 40 then detects, for example, a line of sight direction of the user P1 based on a predetermined radius of curvature of the cornea and the distance between the derived center position of the pupil 62 and the detected reflected image 65 based on a corneal light reflex method.

The detecting unit 40 is not limited to detecting the region 64 including the pupil 62 and the iris 63 based on the characteristic points such as the edges of the contour 61. For example, the detecting unit 40 may derive a correlation between a pupil region template stored beforehand in the EEPROM built into the terminal device 100, and the detected image area of the contour 61 and then detect, as the region 64, an image area in which the derived correlation coefficient exceeds a certain threshold.

The detecting unit 40 is not limited to detecting the line of sight of the user P1 by using the image 50 photographed in a state in which the user P1 is irradiated with an infrared ray. For example, the imaging unit 10 may generate an image that includes color information included in a visible light region by photographing the user P1 irradiated by visible light such as sunlight, and the detecting unit 40 may then detect the line of sight of the user P1 from the image that includes the color information included in the visible light region. In this case, image data of the region 60 extracted from images photographed while the line of sight is extended in various directions, is preferably stored beforehand in a built-in EEPROM and the like. The detecting unit 40 then detects the line of sight of the user P1 by comparing the visible light image photographed with the imaging unit 10 with the various image data stored beforehand.

The region 60 illustrated in FIG. 2 is not limited to the region of the right eye and may also be a region of the left eye.

Figure 3:
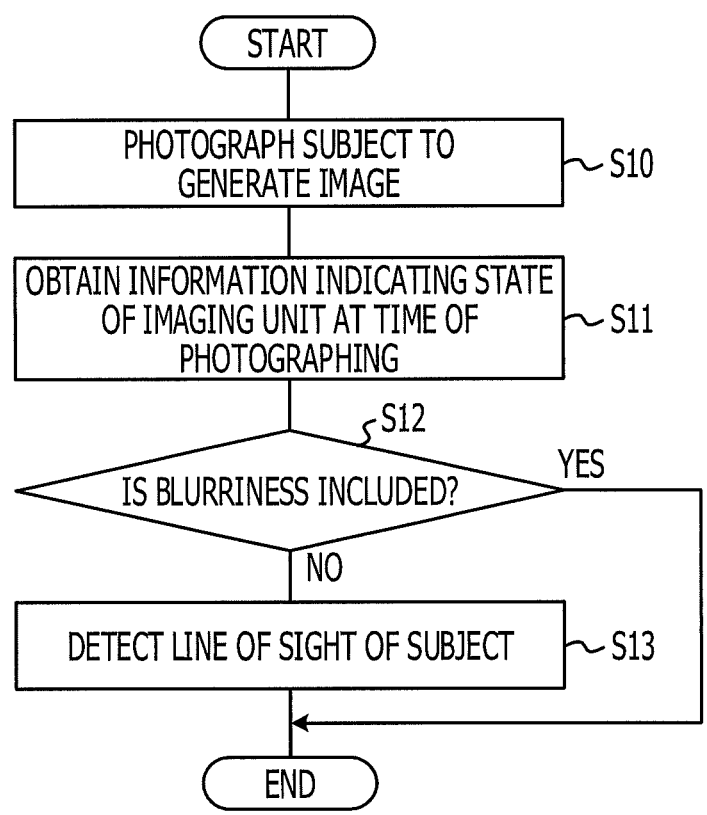
FIG. 3 describes an example of line of sight detection processing of a subject in the terminal device illustrated in FIG. 1.

FIG. 3 describes an example of processing to detect a line of sight of a subject in the terminal device illustrated in FIG. 1. Steps S10, S11, S12 and S13 describe operations of the terminal device 100 and describe examples of a line of sight detection program and a line of sight detection method. For example, the processing described in FIG. 3 is executed by a processor mounted in the terminal device 100 executing a program. The processing described in FIG. 3 may also be executed with hardware mounted in the terminal device 100.

In step S10, the imaging unit 10 photographs the user P1 to generate an image by causing the light source 15 to irradiate an infrared ray on the user P1 who is operating the hand-held terminal device 100. The imaging unit 10 outputs the generated image to the determining unit 30.

In step S11, the obtaining unit 20 then detects a parameter such as angular speed that indicates a change in the orientation of the terminal device 100 at the time of the photographing operation by the imaging unit 10. The obtaining unit 20 obtains the detected parameter as information that indicates the state of the imaging unit 10 when photographing. The obtaining unit 20 outputs the obtained information to the determining unit 30.

In step S12, the determining unit 30 then determines whether the image photographed in step S10 includes blurriness due to shaking of the imaging unit 10 based on the information received from the obtaining unit 20. For example, if the magnitude of the angular speed obtained in step S11 is equal to or greater than a threshold $\alpha$, the determining unit 30 determines that the image photographed in step S10 includes blurriness due camera shake caused by the user P1 the like. If the determining unit 30 determines that the image includes blurriness (YES), the processing series is finished. Conversely, if the magnitude of the angular speed obtained in step S11 is less than the threshold $\alpha$, the determining unit 30 determines that the image photographed in step S10 does not include blurriness. If the determining unit 30 determines that the image does not include blurriness (NO), the determining unit 30 outputs the image to the detecting unit 40 and the processing moves to step S13.

In step S13, the detecting unit 40 receives the image determined as not having blurriness by the determining unit 30 and detects the line of sight of the user P1 who is the subject.

The obtaining unit 20 described in the above embodiment detects a parameter that indicates the orientation state of the terminal device 100 and obtains the detected parameter as information that indicates a condition of the imaging unit 10 when photographing. The determining unit 30 determines whether the image photographed with the imaging unit 10 includes blurriness due to shaking of the imaging unit 10 based on the obtained information, and selectively outputs the image determined as not including blurriness to the detecting unit 40. The detecting unit 40 receives the image determined as not having blurriness even if the terminal device 100 has been operated while being held in the hands of the user P1, and then the detecting unit 40 is able to detect with high precision the reflected image 65 of the cornea from the light source 15 in the region 60 of the eye. As a result, the detecting unit 40 is able to detect the line of sight of a person with high precision.

The terminal device 100 is not limited to being a smartphone or a tablet terminal. The terminal device 10 may also be an on-board terminal device such as a car navigation device. In this case, for example, the determining unit 30 determines whether the image photographed with the imaging unit 10 includes blurriness due to the vehicle vibrating while driving, and then selectively outputs the image determined as not having blurriness to the detecting unit 40. As a result, the detecting unit 40 is better able to detect with high precision the line of sight of the driver who is the subject than in a case in which the line of sight is to be detected from an image that includes blurriness.

Figure 4:
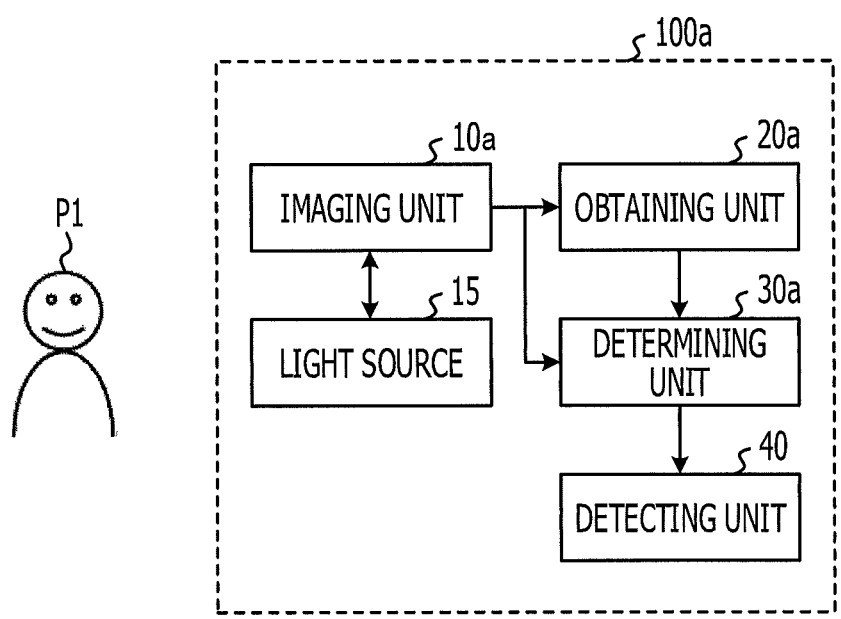
FIG. 4 illustrates another embodiment of a terminal device.

FIG. 4 illustrates another embodiment of the terminal device. A terminal device 100a illustrated in FIG. 4 is, for example, a terminal device such as a smartphone or a tablet device. Elements of the terminal device 100a illustrated in FIG. 4 that have the same or similar functions as the elements illustrated in FIG. 1 are provided with the same reference symbol and explanations thereof will be omitted.

An imaging unit 10a is, for example, a camera that includes an imaging element such as a CCD or a CMOS. For example, the imaging unit 10a causes the light source 15 to irradiate infrared ray light onto the user P1 who is operating the hand-held terminal device 100a, to generate moving image frames by continuously photographing the user P1 at a certain frame rate such as several frames to several tens of frames per second. The imaging unit 10a outputs the generated frames sequentially to an obtaining unit 20a and a determining unit 30a. While the imaging unit 10a photographs the user P1 by causing the light source 15 to irradiate an infrared ray at the user P1, the user P1 may also be photographed without causing the light source 15 to irradiate an infrared ray. The imaging unit 10a is disposed in the terminal device 100a but is not limited thereto. For example, the imaging unit 10a may be disposed outside of the terminal device 100a in a fixed positional relationship with the terminal device 100a. In this case, the imaging unit 10a is preferably connected to the terminal device 100 via a USB standard interface built into the terminal device 100a when photographing the user P1 operating the terminal device 100a.

The obtaining unit 20a obtains information indicating a state of the imaging unit 10a when photographing the subject. For example, the obtaining unit 20a sequentially receives the newest frame photographed with the imaging unit 10a and extracts the brightness and edge information that indicates the characteristics of the edges from the received newest frame and from a received frame photographed before the newest frame. Hereinbelow, the newest frame is referred to as the current frame and a frame photographed before the newest frame is referred to as a past frame. The current frame is an example of a first frame and the past frame is example of a second frame. The edge information and the brightness are examples of a feature quantity.

For example, the obtaining unit 20a associates pixels included in the current frame and the past frame and calculates a difference between the feature quantity of the current frame and the feature quantity of the past frame, and derives an image region in which are dispersed pixels for which the calculated difference between the feature quantities is no equal to or greater than a certain threshold. The obtaining unit 20a outputs, to the determining unit 30a, the magnitude of the derived image region as information that indicates the state of the imaging unit 10a when photographing.

The following is an explanation of the obtaining unit 20a using the magnitude of the derived image region as the information that indicates the state of the imaging unit 10a when photographing. For example, the current frame photographed with the imaging unit 10a is an image that is the same or similar to the past frame if there is no adverse effect such as camera shake caused by the user P1. Specifically, when the dispersion of the feature quantities in the current frame and in the past frame is the same and a difference between the feature quantities of the current frame and the past frame is derived, pixels having values smaller than the certain threshold will be more numerous than pixels having values equal to or greater than the certain threshold. Conversely, if the current frame includes blurriness due to an adverse effect such as camera shake caused by the user P1 for example, the dispersion of the feature quantities in the current frame and the past frame will be different. Specifically, if blurriness is included in the current frame, when the difference between the feature quantities of the current frame and the past frame is derived, the number of pixels for which the difference is equal to or greater than the certain threshold will increase in comparison to when there is no adverse effect due to camera shake caused by the user P1. That is, the obtaining unit 20a uses the magnitude of the derived image region as the information that indicates the state of the imaging unit 10a when photographing after a change of the magnitude of the image region in which are dispersed the pixels for which the difference is equal to or greater than the certain threshold in accordance with the magnitude of the adverse effect due to camera shake caused by the user P1.

While the obtaining unit 20a uses the magnitude of the image region in which are dispersed the pixels for which the difference is equal to or greater than the certain threshold as the information indicating the state of the imaging unit 10a when photographing, the obtaining unit 20a may also use the number of pixels for which the difference is equal to or greater than the certain threshold as the information indicating the state of the imaging unit 10a when photographing.

The certain threshold is preferably determined by testing in the design stage or the manufacturing stage and the like and set to be within a permissible range in which is obtained the precision of the line of sight detection expected for the detecting unit 40.

For example, the determining unit 30a receives the current frame from the imaging unit 10a and receives, from the obtaining unit 20a, the magnitude of the image region for which is derived the information that indicates the state of the imaging unit 10a when the current frame was photographed. The determining unit 30 determines whether the current image photographed with the imaging unit 10a includes blurriness due to shaking of the imaging unit 10a, based on the magnitude of the image region received from the obtaining unit 20a. For example, the determining unit 30a determines that the current frame is an image that includes blurriness due to camera shake caused by the user P1 and the like if the received magnitude of the image region is equal to or greater than a threshold β. The determining unit 30a, for example, then discards the current frame determined as including blurriness. Conversely, if the magnitude of the image region is less than the threshold β, the determining unit 30a determines that the current frame does not include blurriness and outputs the current frame to the detecting unit 40.

The threshold β is preferably determined by testing in the design stage or the manufacturing stage and the like and set to be within a permissible range in which is obtained the precision of the line of sight detection expected for the detecting unit 40. Moreover, the magnitude of the image region obtained by the obtaining unit 20a differs if the user P1 is operating the terminal device 100a while sitting in a chair and the like or if the user P1 is operating the terminal device 100a while on board a bus or a train and the like. Accordingly, the user P1 may appropriately set the threshold β in correspondence to the environment by using a keyboard or touch panel provided on the terminal device 100a to select an operating environment of the terminal device 100a.

The determining unit 30a is not limited to determining whether the received current frame includes blurriness by comparing the received magnitude of the image region with the threshold β. For example, the obtaining unit 20a detects the region 64 of the pupil or the reflected image 65 that represent a certain location in the user P1 from the received current frame in the same way as the detecting unit 40, to derive a shape of the detected region 64 or the reflected image 65. The obtaining unit 20a obtains a strain amount that indicates a degree of strain of a shape such as an oval shape that indicates the derived region 64 or the reflected image 65 and that is associated with the shape such as an oval shape that indicates the derived region 64 or the reflected image 65 from an image that does not include blurriness, as the information that indicates the state of the imaging unit 10a when photographing. The determining unit 30a may then determine whether the current frame includes blurriness based on the comparison between the derived strain amount and a certain value.

Figure 5:
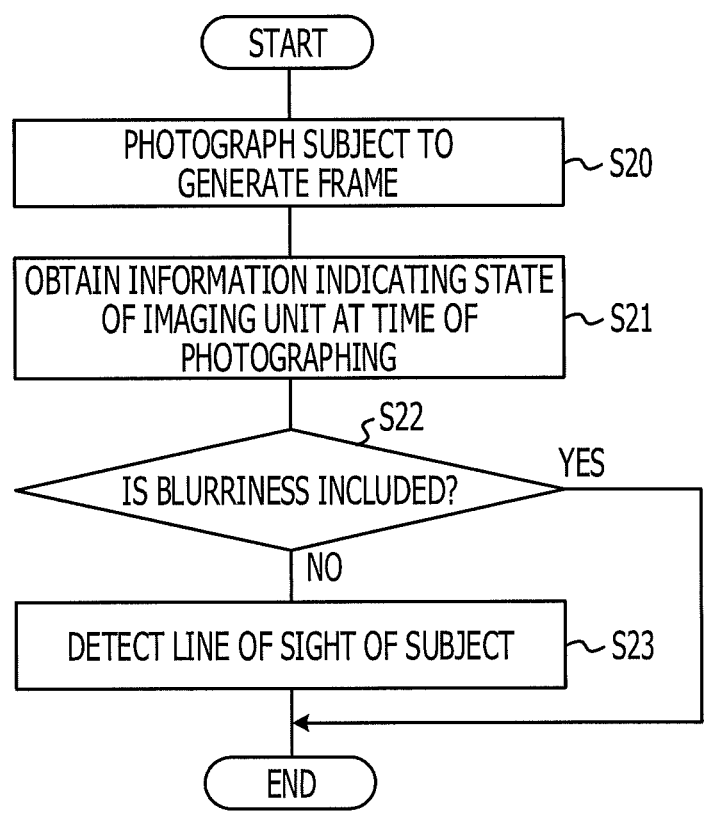
FIG. 5 describes an example of line of sight detection processing of a subject in the terminal device illustrated in FIG. 4.

FIG. 5 describes an example of processing to detect a line of sight of a subject in the terminal device 100a illustrated in FIG. 4. Steps S20, S21, S22 and S23 describe operations of the terminal device 100a and describe examples of the line of sight detection program and the line of sight detection method. For example, the processing described in FIG. 5 is executed by a processor mounted in the terminal device 100a executing a program. The processing described in FIG. 5 may also be executed with hardware mounted in the terminal device 100a. The processing illustrated in FIG. 5 is preferably repeated for each frame generated by the user P1 photographing at a certain frame rate.

In step S20, the imaging unit 10a generates a frame by causing the light source 15 to irradiate an infrared ray on the user P1 who is operating the hand-held terminal device 100a and by photographing the user P1 at a certain frame rate. The imaging unit 10a sequentially outputs the generated frame to the obtaining unit 20a and the determining unit 30a as the current frame.

In step S21, the obtaining unit 20a receives the current frame from the imaging unit 10a and extracts feature quantities such as edge information or brightness from the current frame and from a past frame photographed before the current frame. The obtaining unit 20a associates the pixels included in the current frame and the past frame and calculates a difference between the extracted feature quantity of the current frame and the extracted feature quantity of the past frame to derive an image region in which are dispersed pixels for which the calculated difference between the feature quantities is no less than a certain threshold. The obtaining unit 20a outputs, to the determining unit 30a, the magnitude of the derived image region as information that indicates the state of the imaging unit 10a when photographing.

In step S22, the determining unit 30a then determines whether the current frame photographed in step S20 includes blurriness due to shaking of the imaging unit 10a based on the information received from the obtaining unit 20a. For example, the determining unit 30a determines that the current frame photographed in step S20 includes blurriness due to camera shake caused by the user P1 if the magnitude of the image region obtained in step S21 is equal to or greater than the threshold β. If the determining unit 30a determines that the current frame includes blurriness (YES), the processing series is finished. Conversely, if the determining unit 30a determines that the current frame photographed in step S20 does not include blurriness if the magnitude of the image region obtained in step S21 is less than the threshold β. The determining unit 30a then determines that the current frame does not include blurriness (NO) and outputs the current frame to the detecting unit 40 and the processing moves to step S23.

In step S23, the detecting unit 40 receives the current frame determined as not having blurriness by the determining unit 30a and detects the line of sight of the user P1 who is the subject.

As described above in the present embodiment, the obtaining unit 20a obtains information that indicates a condition of the imaging unit 10a while photographing based on the difference between the feature quantities such as edge information or brightness extracted from the current frame and the past frame. The determining unit 30a determines whether the frame photographed with the imaging unit 10a includes blurriness based on the obtained information, and selectively outputs the frame determined as not including blurriness to the detecting unit 40. The detecting unit 40 receives the frame determined as not including blurriness even if the terminal device 100a has been operated while being held in the hands of the user P1, and then the detecting unit 40 is able to detect with high precision the reflected image 65 of the cornea from the light source 15 in the region 60 of the eye. As a result, the detecting unit 40 is able to detect the line of sight of a person with high precision.

The terminal device 100a is not limited to being a smartphone or a tablet terminal. The terminal device 100a may also be an on-board terminal device such as a car navigation device. In this case, for example, the determining unit 30a determines whether the image photographed with the imaging unit 10a includes blurriness due to the vehicle vibrating while driving, and then selectively outputs the image determined as not including blurriness to the detecting unit 40. As a result, the detecting unit 40 is better able to detect with high precision the line of sight of the driver who is the subject than in a case in which the line of sight is to be detected from an image that includes blurriness.

Figure 6:
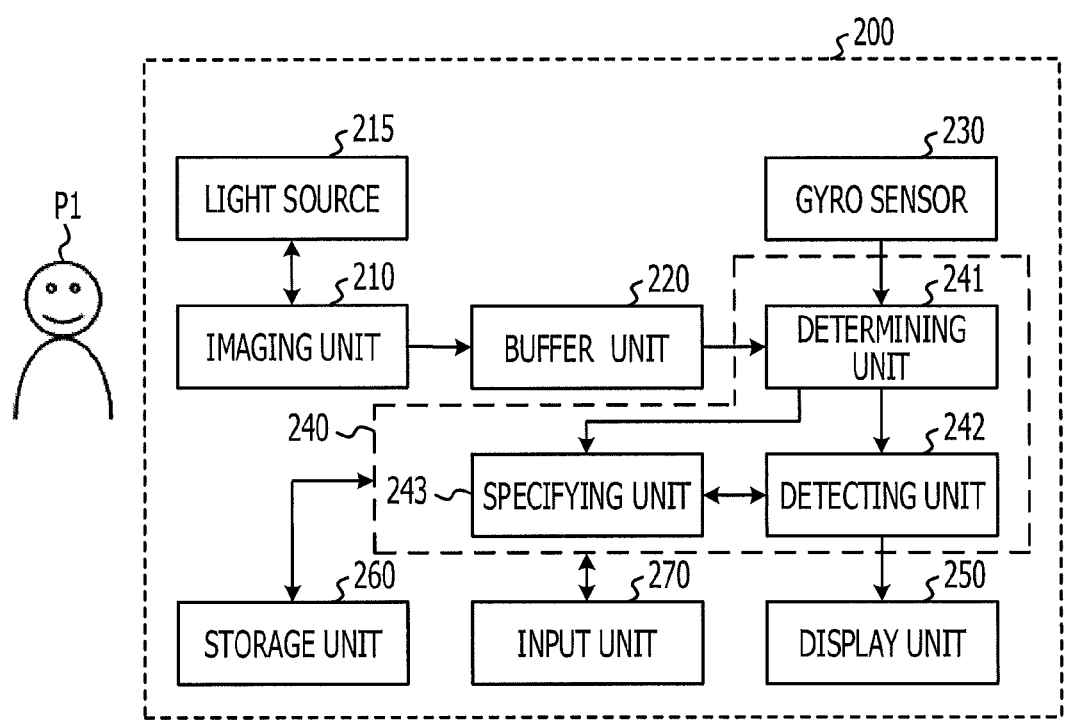
FIG. 6 illustrates another embodiment of a terminal device.

FIG. 6 illustrates another embodiment of the terminal device. A terminal device 200 illustrated in FIG. 6 is a terminal device such as a smartphone or a tablet terminal for example, and includes an imaging unit 210, a light source 215, a buffer unit 220, a gyro sensor 230, a control unit 240, a display unit 250, a storage unit 260, and an input unit 270.

The imaging unit 210 is, for example, a camera that includes an imaging element such as a CCD or a CMOS. For example, the imaging unit 210 causes the light source 215 which is an LED that emits an infrared ray to irradiate an infrared ray onto the user P1 who is operating the hand-held terminal device 200, to generate moving image frames by continuously photographing the user P1 at a certain frame rate such a several frames to several tens of frames per second. The imaging unit 210 sequentially outputs the generated frames to the buffer unit 220.

The buffer unit 220 is a random access memory (RAM) and the like and sequentially receives and stores the generated frames from the imaging unit 210. The buffer unit 220 outputs the stored frames to the control unit 240.

The gyro sensor 230 detects a parameter such as angular speed that indicates changes in the orientation of the terminal device 200, and obtains information that indicates the state of the imaging unit 210 while photographing. The gyro sensor 230 outputs the obtained information to the control unit 240. The gyro sensor 230 is an example of an obtaining unit.

The control unit 240 includes a processor that executes a program stored in the storage unit 260 such as an EEPROM for example, and controls the parts of the terminal device 200. A determining unit 241, a detecting unit 242, and a specifying unit 243 are realized by the control unit 240 executing a line of sight detection program stored in the storage unit 260.

The determining unit 241 reads, for example, a frame photographed by the imaging unit 210 from the buffer unit 220 and determines whether the read frame includes blurriness due to shaking of the imaging unit 210 based on the information received from the gyro sensor 230. For example, the determining unit 241 determines that the read frame is an image that includes blurriness if the magnitude of the angular speed is equal to or greater than a threshold $\alpha 1$ from the information received from the gyro sensor 230 at the time that the read frame was photographed. The determining unit 241 then outputs the read frame to the specifying unit 243. Conversely, the determining unit 241 determines that the read frame does not include blurriness if the magnitude of the angular speed is less than the threshold $\alpha 1$, and the outputs the frame to the detecting unit 242.

The threshold $\alpha 1$ is preferably set according to a magnitude of the angular speed that is determined by testing in the design stage or the manufacturing stage and the like, within a permissible range in which is obtained the precision of the line of sight detection expected for the detecting unit 242. Moreover, the magnitude of the angular speed detected by the gyro sensor 230 differs if the user P1 is operating the terminal device 200 while sitting in a chair and the like or if the user P1 is operating the terminal device 200 while on board a bus or a train and the like. Accordingly, the user P1 may appropriately set the threshold al in correspondence with the environment by using the input unit 270 such as a keyboard or touch panel to select the operating environment of the terminal device 200.

The detecting unit 242 receives the frame determined as not including blurriness by the determining unit 241 and detects the line of sight of the user P1 who is the subject. The line of sight detection processing by the detecting unit 242 is the same or similar to that of the detecting unit 40 illustrated in FIG. 1 when using the received frame as the image 50 illustrated in FIG. 2A, and therefore an explanation thereof will be omitted. The detecting unit 242 outputs, to the specifying unit 243, image data of the region 60 that includes, for example, the eye as illustrated in FIGS. 2A and 2B detected from the frame that is determined as not including blurriness by the determining unit 241.

The specifying unit 243 receives from the detecting unit 242, for example, the frame determined as including blurriness by the determining unit 241 and also receives image data of the region 60 in a frame determined as not including blurriness photographed before the received frame. The specifying unit 243 derives a correlation between the frame that includes blurriness received from the determining unit 241, for example, and the region 60 received from the detecting unit 242. The specifying unit 243 specifies an image region in the frame that includes blurriness as a region that includes the eye corresponding to the region 60 if the derived correlation coefficient exceeds a certain threshold. The specifying unit 243 the outputs, to the detecting unit 242, the specified image data of the region that includes the eye in the frame that includes the blurriness. The detecting unit 242, for example, derives a correlation between a subsequent frame, for example, determined as not having blurriness by the determining unit 241 and the image data of the region that includes the eye received from the specifying unit 243. The detecting unit 242 detects an image region in the subsequent frame for which the derived correlation coefficient exceeds a certain threshold, as the region 60 illustrated in FIG. 2. As a result, the detecting unit 242 is able to omit the processing for detecting the face and the eye and thus the line of sight detection processing in the terminal device 200 may be performed at a high speed.

The display unit 250 is a display such as an organic electroluminescent (EL) display or a liquid crystal display, and displays text and images and the like and detection results obtained by the detecting unit 242 based on, for example, control instructions from the control unit 240.

Figure 7:
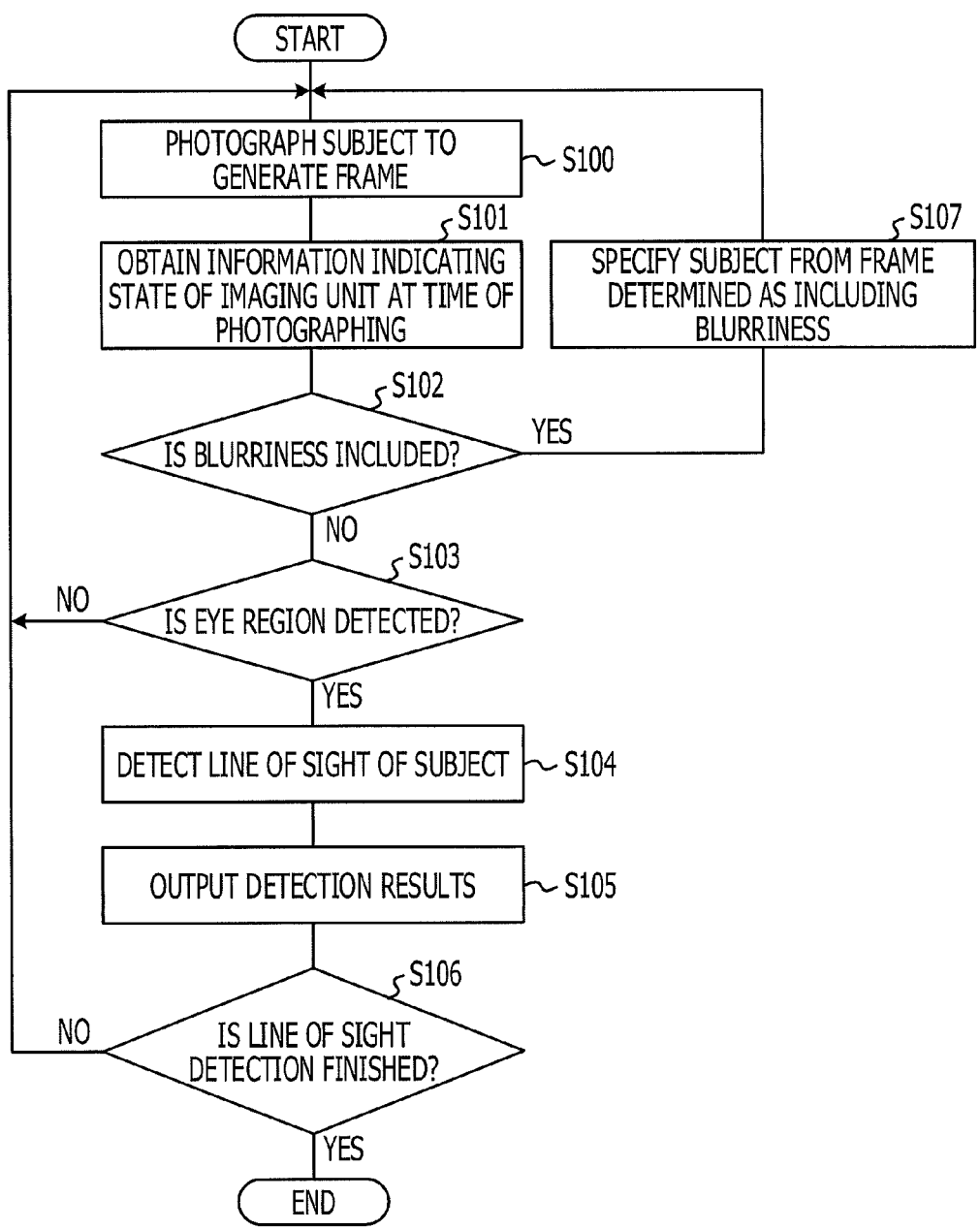
FIG. 7 describes an example of line of sight detection processing of a subject in the terminal device illustrated in FIG. 6.

FIG. 7 describes an example of processing to detect a line of sight of a subject in the terminal device 200 illustrated in FIG. 6. Steps S100 to S107 illustrate operations by the terminal device 200 and illustrate examples of the line of sight detection program and the line of sight detection method. For example, the processing described in FIG. 7 is executed by a processor mounted in the terminal device 200 executing a program. The processing described in FIG. 7 may also be executed with hardware mounted in the terminal device 200. The processing illustrated in FIG. 7 is preferably repeated for each frame generated by imaging unit 210 while the user P1 is photographing at a certain frame rate.

In step S100, the imaging unit 210 generates a frame by causing the light source 215 to irradiate an infrared ray on the user P1 who is operating the hand-held terminal device 200 and by photographing the user P1 at the certain frame rate. The imaging unit 210 sequentially outputs the generated frames to the buffer unit 220. The buffer unit 220 stores the received frames.

In step S101, the gyro sensor 230 detects a parameter such as the angular speed that indicates changes in the orientation of the terminal device 200 while the imaging unit 210 is photographing. The gyro sensor 230 outputs the detected parameter as information that indicates the state of the imaging unit 210 when photographing, to the determining unit 241, and the processing moves to step S102.

In step S102, the determining unit 241 determines whether the frame photographed in step S100 includes blurriness due to shaking of the imaging unit 210 based on the information received from the gyro sensor 230. For example, the determining unit 241 reads the frame photographed in step S100 from the buffer unit 220. The determining unit 241 determines that the read frame includes blurriness due to camera shake caused by the user P1 and the like if the magnitude of the angular speed detected in step S101 is equal to or greater than the threshold α1. If the read frame is determined as including blurriness (YES), the determining unit 241 then outputs the frame to the specifying unit 243 and the processing moves to step S107. Conversely, the determining unit 241 determines that the read frame does not include blurriness if the magnitude of the angular speed detected in step S101 is smaller than the threshold α1. If the read frame is determined as not including blurriness (NO), the determining unit 241 then outputs the frame to the detecting unit 242 and the processing moves to step S103.

In step S103, the detecting unit 242 receives the frame determined as not including blurriness by the determining unit 241 and determines whether the received frame includes the region 60 that includes the eye. For example, the detecting unit 242 extracts characteristic points such as edges in the image 50 illustrated in FIG. 2A which is the frame received from the determining unit 241, and specifies edge points of the eyebrows, the eyes, the nose, the lips and the like based on the dispersion of the extracted characteristic points. The detecting unit 242 then detects the region 51 based on the positions of the specified edge points. The detecting unit 242 detects the region 60 including the eye based on the information such as the edge points of the eye specified during the extraction of the region 51. If the detecting unit 242 detects the region 60 (YES), the processing moves to step S104. Conversely, if the detecting unit 242 does not detect the region 60 due to, for example, the eye of the user P1 being closed, the user P1 facing sideways, or the user P1 not being photographed (NO), the processing moves to step S100.

The detecting unit 242 may, for example, derive a correlation between the frame received from the determining unit 241 and a template of an image of the face or the eye stored beforehand in the storage unit 260, and detect an image region in which the derived correlation coefficient exceeds a certain threshold as the region 51 or the region 60.

The detecting unit 242 receives image data of the region that includes the eye from the specifying unit 243 for example, and then if a subsequent frame determined as not including blurriness by the determining unit 241 is received, the detecting unit 242 derives a correlation between the subsequent frame and the image data of the region received from the specifying unit 243. The detecting unit 242 may detect an image region in the subsequent frame for which the derived correlation coefficient exceeds the certain threshold, as the region 60. As a result, the detecting unit 242 is able to detect the region 60 quickly by omitting the detection processing of the face or the eye.

In step S104, the detecting unit 242 detects the contour 61 of the eye based on the specified edge points of the eye when the region 60 is detected, in the region 60 detected in step S103 for example. The detecting unit 242 then detects a region in the image region inside the detected contour 61 in which, for example, the characteristic points such as edges are dispersed in a circular shape and a brightness value of the circular region is lower than a brightness value of the surrounding regions, as the region 64 that includes the pupil 62 and the iris 63. The detecting unit 242 derives the center position of the pupil 62 from the detected region 64. The detecting unit 242 further detects a light spot that indicates the position where the infrared ray irradiated from the light source 215 is reflected by the cornea of the eye of the user P1, as the reflected image 65 of the light source 215 due to the cornea having a brightness value equal to or greater than a certain threshold and having a round shape in the region 64. The detecting unit 242 then detects, for example, a line of sight direction of the user P1 based on a predetermined radius of curvature of the cornea and the distance between the derived center position of the pupil 62 and the detected reflected image 65 based on a corneal light reflex method. The detecting unit 242 then outputs the image data of the detected region 60 to the specifying unit 243.

Next in step S105, the detecting unit 242 outputs the detection result of the line of sight of the user P1. For example, the control unit 240 controls the display of the display unit 250 based on the received detection result. The control unit 240 derives the distance between the terminal device 200 and the user P1 from, for example, the magnitude of the region 51 detected in step S103. The control unit 240 derives the position at which the user P1 is looking on the display screen of the display unit 250 based on the derived distance and the detected line of sight direction of the user P1 in step S104. The control unit 240, for example, outputs to the display unit 250 a control instruction to specify the derived position as the display position of a cursor to cause the display unit 250 to move the displayed cursor. The control unit 240 may select an icon displayed at the derived position. Alternatively, the control unit 240 may enlarge the display of a certain region centered on the derived position and display the enlarged display on the display unit 250.

Next, in step S106, the control unit 240 determines, for example, whether an instruction to finish the line of sight detection of the user P1 has been received via the input unit 270. The control unit 240 finishes the processing series if the finish instruction has been received (YES). Conversely, the processing moves to step S100 if the control unit 240 has not received the finish instruction (NO).

In step S107, the specifying unit 243 receives the frame determined as including blurriness from the determining unit 241 and also receives, from the detecting unit 242, the image data of the region 60 in a frame determined as not having blurriness and photographed before the received frame. The specifying unit 243 performs correlation processing between the frame that includes blurriness received from the determining unit 241 and the region 60 received from the detecting unit 242. In this case, the correlation processing refers to processing for deriving a level of similarity between images (which may also be referred to as between frames). The correlation between images involves the use of a known normalized cross-relation $R_{NCC}$ as expressed in the following equation for the calculation. In the following equation, the brightness value of one of the images is represented as T(i, j) and the brightness value of the other image is represented as I(i, j).

$$R_{NCC} = \frac{\sum_{j=0}^{N-1}\sum_{i=0}^{M-1} I(i, j)T(i, j)}{\sqrt{\sum_{j=0}^{N-1}\sum_{i=0}^{M-1} I(i, j)^2 \times \sum_{j=0}^{N-1}\sum_{i=0}^{M-1} T(i, j)^2}} \quad \text{(Equation 1)}$$

The above normalized cross-relation $R_{NCC}$ may be referred to as a correlation coefficient. The correlation coefficient takes on a value between −1 and 1 when the normalized cross-relation $R_{NCC}$ is used. Next, the specifying unit 243 specifies an image region in which the derived correlation coefficient exceeds a certain threshold (e.g., 0.8) as a region that includes the eye corresponding to the region 60 in the frame that includes the blurriness. The specifying unit 243 then outputs, to the detecting unit 242, the specified image data of the region that includes the eye in the frame that includes the blurriness. Next, the control unit 240 moves to the processing in step S100 and conducts the processing in steps S100 to S106 on a subsequent frame photographed by the imaging unit 210. As described above, the specifying unit 243 is able to specify the region 60 in the frame including blurriness. If the subsequent frame does not include blurriness, the detection of the line of sight in the frame may be conducted at a high speed. In other words, since the position of the eye region may be specified in the subsequent frame when the position of the eye region (region 60) in a frame is known, the processing to search for the eye region throughout the entire region in the subsequent frame may be reduced.

The gyro sensor 230 described in the above embodiment detects a parameter that indicates the orientation state of the terminal device 200 and obtains the detected parameter as information that indicates a condition of the imaging unit 210 while photographing. The determining unit 242 determines whether the frame photographed with the imaging unit 210 includes blurriness based on the obtained information, and selectively outputs a frame determined as not including blurriness to the detecting unit 242. The detecting unit 242 receives the frame determined as not including blurriness even if the terminal device 200 has been operated while being held in the hands of the user P1, and then the detecting unit 242 is able to detect with high precision the reflected image 65 of the cornea from the light source 215 in the region 60 of the eye. As a result, the detecting unit 242 is able to detect the line of sight of a person with high precision.

Moreover, the specifying unit 243 specifies the region that includes the eye from the frame determined as including blurriness, and the detecting unit 242 detects the region 60 in a subsequent frame that is determined as not including blurriness based on the specified region. As a result, the detecting unit 242 is able to omit the processing to detect the face or the eye and is able to perform the line of sight detection processing at a high speed.

The terminal device 200 is not limited to being a smartphone or a tablet terminal. The terminal device 200 may also be an on-board terminal device such as a car navigation device. The determining unit 242 then determines, for example, whether the frame photographed with the imaging unit 210 includes blurriness based on vibration when the vehicle is being driven, and outputs the frame determined as not including blurriness to the detecting unit 242. As a result, the detecting unit 242 is better able to detect with high precision the line of sight of a driver who is the subject than in a case in which the line of sight is to be detected from an image that includes blurriness.

While the terminal device 200 has the gyro sensor 230, the terminal device 200 is not limited thereto and may have an acceleration sensor.

While the threshold α1 of the determining unit 241 is a value determined by testing during the design stage or the manufacturing stage or is a value selected by the user P1 in accordance with the environment in which the terminal device 200 is being operated, the threshold α1 is not limited thereto. For example, the determining unit 241 may assume an environment in which the terminal device is being operated based on the magnitude of an angular speed and the like detected by the gyro sensor 230, and then set the value determined based on the assumed environment as the threshold α1.

The detecting unit 242 is not limited to using frames photographed by irradiating the user P1 with an infrared ray to detect the line of sight of the user P1. For example, the imaging unit 210 may generate a frame including color information included in a visible light region by photographing the user P1 irradiated with visible light from sunlight and the like, and the detecting unit 242 may detect the line of sight of the user P1 from the frame including the color information included in the visible light region. In this case, the storage unit 260 preferably stores the image data of the region 60 extracted from images photographed while the line of sight is extended in various directions. The detecting unit 242 then detects the line of sight of the user P1 by comparing the visible light frame photographed with the imaging unit 210 with the various image data stored beforehand.

The detecting unit 242 is not limited to performing the line of sight detection processing on all the frames determined as not including blurriness. For example, the detecting unit 242 may perform the line of sight detection processing by reducing the number of the received frames when frames determined as not including blurriness are received continuously from the determining unit 241. However, the number of frames to be reduced is preferably set as appropriate in accordance with the frame rate of the imaging unit 210.

The control unit 240 is not limited to controlling the display unit 250 based on the direction of the line of sight of the user P1 detected by the detecting unit 242. For example, the control unit 240 may output the result of the line of sight detection to an external computer and the like through wireless communication such as a wireless local area network (LAN) or the wireless fidelity (Wi-Fi) standard built into the terminal device 200. As a result, the external computer is able to obtain information about images and articles of interest to the user P1 among the information displayed on the display unit 250 from the line of sight detection result, and the external computer may provide information appropriate to the user P1 based on the obtained information.

Figure 8:
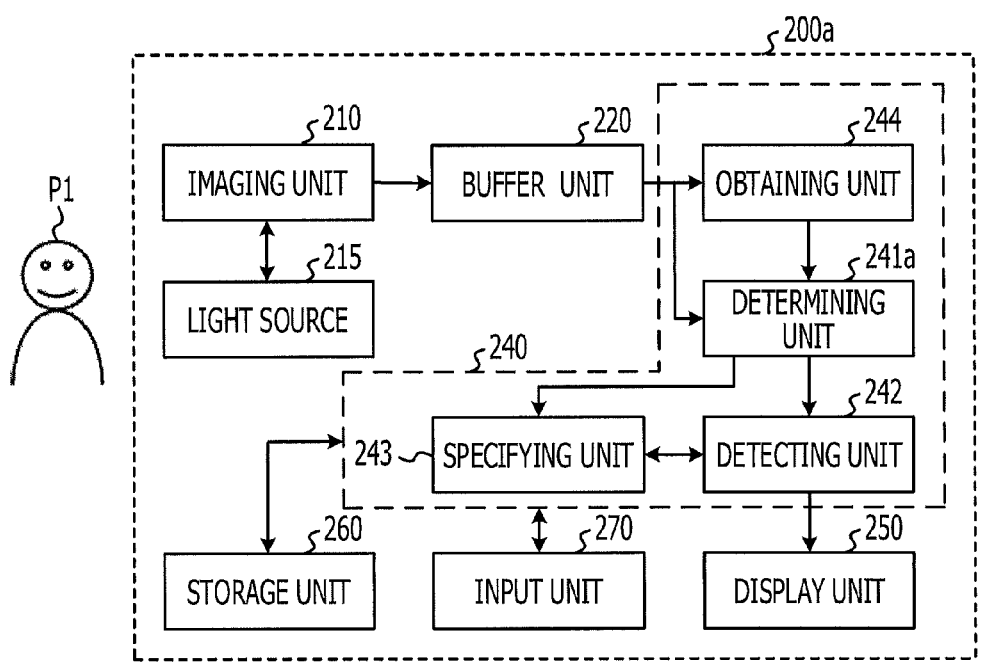
FIG. 8 illustrates another embodiment of a terminal device.

FIG. 8 illustrates another embodiment of the terminal device. A terminal device 200a illustrated in FIG. 8 is, for example, a terminal device such as a smartphone or a tablet device. Elements of the terminal device 200a illustrated in FIG. 8 that have the same or similar functions as the elements illustrated in FIG. 6 are provided with the same reference symbol and explanations thereof will be omitted.

An obtaining unit 244 obtains information indicating a state of the imaging unit 210 when photographing the subject. For example, the obtaining unit 244 reads, from the buffer unit 220, the newest frame photographed by the imaging unit 210 and a frame photographed one frame earlier. Hereinbelow, the newest frame is referred to as the current frame and frame photographed one frame before the newest frame is referred to as the past frame.

For example, the obtaining unit 244 extracts the feature quantities such as brightness and edge information that indicates the edge characteristics from the read current frame and the past frame. The obtaining unit 244 associates the pixels included in the current frame and the past frame and calculates an absolute value of a difference between the extracted feature quantity of the current frame and the extracted feature quantity of the past frame, and derives an image region in which are dispersed pixels for which the calculated absolute value of the difference is no less than a threshold $\epsilon$. The obtaining unit 244 outputs, to the determining unit 241a, the derived magnitude of the image region as information that indicates the state of the imaging unit 210 when photographing. The obtaining unit 244 may output, to the determining unit 241a, the derived number of pixels included in the image region as information that indicates the state of the imaging unit 210 when photographing in place of the derived magnitude of the image region. The threshold $\epsilon$ is preferably determined by testing in the design stage or the manufacturing stage and the like and set to be within a permissible range that encompasses the precision of the line of sight detection expected for the detecting unit 242.

The determining unit 241a reads the current frame from the buffer unit 220 and receives the magnitude of the image region from the obtaining unit 244. For example, the determining unit 241a determines whether the current frame includes blurriness due to shaking of the imaging unit 210 based on the received magnitude of the image region. The determining unit 241a determines that the received current frame is an image that includes blurriness due to camera shake caused by the user P1 and the like, for example, if the received magnitude of the image region is equal to or greater than a threshold $\beta1$. The determining unit 241a then outputs the current frame determined as including blurriness to the specifying unit 243. Conversely, if the magnitude of the image region is less than the threshold $\beta1$, the determining unit 241a determines that the current frame does not include blurriness and outputs the current frame to the detecting unit 242.

The threshold $\beta1$ is preferably determined by testing in the design stage or the manufacturing stage and the like and set to be within a permissible range that encompasses the precision of the line of sight detection expected for the detecting unit 242. Moreover, the magnitude of the image region obtained by the obtaining unit 241a differs if the user P1 is operating the terminal device 200 while sitting in a chair and the like or if the user P1 is operating the terminal device 200 while on board a bus or a train and the like. Accordingly, the user P1 may appropriately set the threshold $\beta1$ in correspondence with the environment by using the input unit 270 such as a keyboard or touch panel to select the operating environment of the terminal device 200.

The determining unit 241a may receive from the obtaining unit 244 the number of images included in the image region as the information that indicates the state of the imaging unit 210 when photographing. Specifically, the determining unit 241a may determine whether the current frame includes blurriness due to shaking of the imaging unit 210 based on the received number of images included in the image region.

Since the past frame of one frame earlier does not exist before the frame first photographed by the imaging unit 210, the obtaining unit 244 and the determining unit 241a treat the frame first photographed as an image without blurriness.

Figure 9:
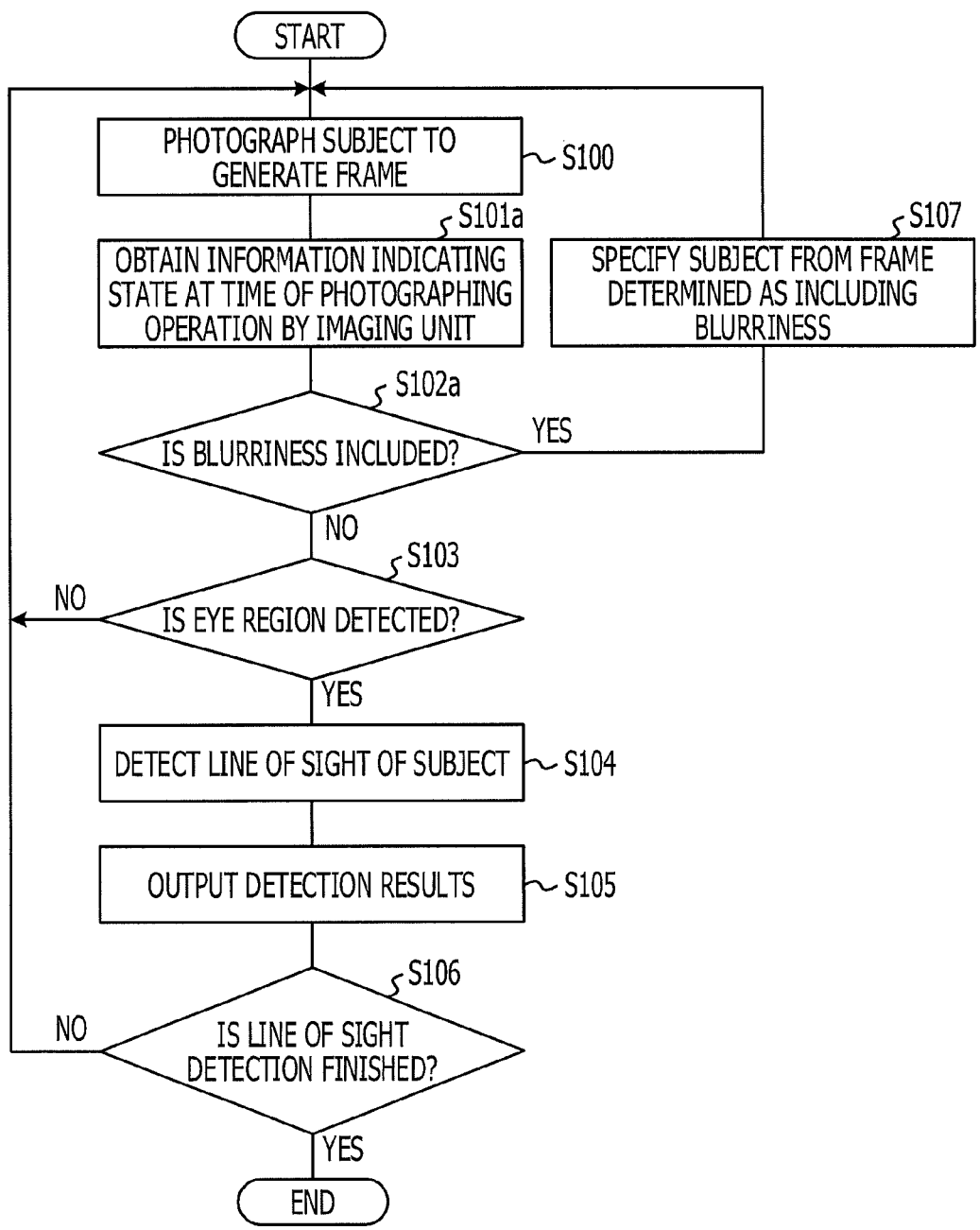
FIG. 9 describes an example of line of sight detection processing of a subject in the terminal device illustrated in FIG. 8.

FIG. 9 describes an example of processing to detect the line of sight of a subject in the terminal device 200a illustrated in FIG. 8. Steps S100, S101, S102 and S103, S104, S105 and S106 describe operations of the terminal device 200a and describe examples of the line of sight detection program and the line of sight detection method. For example, the processing described in FIG. 9 is executed by a processor mounted in the terminal device 200a executing a program. The processing described in FIG. 9 may also be executed with hardware mounted in the terminal device 200a.

Processing in the steps illustrated in FIG. 9 that is the same as or similar to that of the steps illustrated in FIG. 7 is provided with the same step number and explanations thereof will be omitted.

In step S101a, the obtaining unit 244 reads the current frame photographed by the imaging unit 210 in step S100 and the past frame that is one frame earlier, from the buffer unit 220. The obtaining unit 244 extracts the feature quantities such as brightness and edge information from the read current frame and the past frame. The obtaining unit 244 associates the pixels included in the current frame and the past frame and calculates an absolute value of a difference between the extracted feature quantity of the current frame and the extracted feature quantity of the past frame. The obtaining unit 244 derives an image region in which are dispersed pixels for which the calculated absolute value of the difference is no less than the threshold $\epsilon$. The obtaining unit 244 outputs, to the determining unit 241a, the derived magnitude of the image region as information that indicates the state of the imaging unit 210 when photographing, and the processing moves to step S102a.

In step S102a, the determining unit 241a determines whether the current frame photographed in step S100 includes blurriness due to shaking of the imaging unit 210 based on the information received from the obtaining unit 244. For example, the determining unit 241a reads the current frame from the buffer unit 220 and receives the magnitude of the image region from the obtaining unit 244. For example, the determining unit 241a determines that the current frame includes blurriness due to camera shake caused by the user P1 and the like if the magnitude of the image region received in step S101a is equal to or greater than the threshold $\beta1$. If it is determined that the current frame includes blurriness (YES), the determining unit 241a then outputs the current frame to the specifying unit 243 and the processing moves to step S106. Conversely, the determining unit 241a determines that the current frame does not include blurriness if the magnitude of the image region received in step S101a is less than the threshold β1. The determining unit 241a then determines that the current frame does not include blurriness (NO) and outputs the current frame to the detecting unit 242 and the processing moves to step S103.

As described above in the present embodiment, the obtaining unit 244 obtains information that indicates a condition of the imaging unit 210 while photographing based on an absolute value of the difference between the feature quantities such as edge information or brightness extracted from the current frame and the past frame. The determining unit 241a determines whether the frame photographed with the imaging unit 210 includes blurriness based on the obtained information, and selectively outputs the frame determined as not including blurriness to the detecting unit 242. As a result, the detecting unit 242 is able to detect with high precision the reflected image 65 of the light source 215 due to the cornea from the region 60 of the eye even if the hand-held terminal device 200a is being operated by the user P1. As a result, the detecting unit 242 is able to detect the line of sight of a person with high precision.

Moreover, the specifying unit 243 specifies the region that includes the eye from the frame determined as including blurriness, and the detecting unit 242 detects the region 60 in a subsequent frame that is determined as not including blurriness based on the specified region. As a result, the detecting unit 242 is able to omit the processing to detect the face or the eye and is able to perform the line of sight detection processing at a high speed.

The terminal device 200a is not limited to being a smartphone or a tablet terminal. The terminal device 200a may also be an on-board terminal device such as a car navigation device. The determining unit 241a then determines, for example, whether the frame photographed with the imaging unit 210 includes blurriness based on vibration when the vehicle is being driven, and outputs the frame determined as not including blurriness to the detecting unit 242. As a result, the detecting unit 242 is better able to detect with high precision the line of sight of the driver who is the subject than in a case in which the line of sight is to be detected from an image that includes blurriness.

The determining unit 241a, the detecting unit 242, the specifying unit 243, and the obtaining unit 244 are not limited to processing the frames photographed and generated by the imaging unit 210 at the image size in which they are generated. For example, the control unit 240 may reduce the frames generated by the imaging unit 210 at a reduction ratio of one over four, and the determining unit 241a, the detecting unit 242, the specifying unit 243, and the obtaining unit 244 may process the reduced frames. The processing of the determining unit 241a, the detecting unit 242, the specifying unit 243, and the obtaining unit 244 may be performed at a high speed due to the number of pixels being reduced when the frames are reduced in size.

The obtaining unit 244 is not limited to using the feature quantities of the current frame and the past frame throughout the entire image for obtaining the information that indicates the state of the imaging unit 210 while photographing to obtain the information that indicates the state while the imaging unit 210 is photographing. For example, the obtaining unit 244 may use the feature quantities extracted from the image data of the regions 60 in the current frame and the past frame to obtain the information that indicates the state while the imaging unit 210 is photographing. As a result, processing of the obtaining unit 244 may be performed at high speed since the range for extracting the feature quantities and for deriving the absolute value of the differences of the feature quantities is in the range of the region 60.

While the threshold β1 of the determining unit 241a is a value determined by testing during the design stage or the manufacturing stage or is a value selected by the user P1 in accordance with the environment in which the terminal device 200 is being operated, the threshold β1 is not limited thereto. For example, the determining unit 241a may assume the environment in which the terminal device 200a is being operated based on a parameter such as angle of inclination, angular speed, or acceleration detected by a gyro sensor or an acceleration sensor built into the terminal device 200a. The determining unit 241a may then set a value determined based on the assumed environment as the threshold β1.

The detecting unit 242 is not limited to using frames photographed by irradiating the user P1 with an infrared ray to detect the line of sight of the user P1. For example, the imaging unit 210 may generate a frame including color information included in a visible light region by photographing the user P1 irradiated with visible light from sunlight and the like, and the detecting unit 242 may detect the line of sight of the user P1 from the frame including the color information included in the visible light region. In this case, the storage unit 260 preferably stores the image data of the region 60 extracted from images photographed while the line of sight is extended in various directions. The detecting unit 242 then detects the line of sight of the user P1 by comparing the visible light frame photographed with the imaging unit 210 with the various image data stored beforehand.

The detecting unit 242 may perform the line of sight detection processing by reducing the number of the received images when frames determined as not having blurriness are received continuously from the determining unit 241a. However, the number of frames to be reduced is preferably set as appropriate in accordance with the frame rate of the imaging unit 210.

The determining unit 241a is not limited to determining whether the received current frame includes blurriness by comparing the received magnitude of the image region with the threshold β1. For example, the obtaining unit 241a detects the region 64 of the pupil or the reflected image 65 that represents a certain location in the user P1 from the received current frame in the same way as the detecting unit 242, to derive a shape of the detected region 64 or the reflected image 65. The obtaining unit 244 obtains a strain amount that indicates a degree of strain of a shape such as an oval shape that indicates the derived region 64 or the reflected image 65 and that is associated with the shape such as an oval shape that indicates the derived region 64 or the reflected image 65 from an image that does not include blurriness, as the information that indicates the state of the imaging unit 210 when photographing. The determining unit 241a may then determine whether the current frame includes blurriness based on the comparison between the derived strain amount and a certain value.

The control unit 240 is not limited to controlling the display unit 250 based on the direction of the line of sight of the user P1 detected by the detecting unit 242. For example, the control unit 240 may output the result of the line of sight detection to an external computer and the like through wireless communication such as a wireless LAN or the Wi-Fi standard built into the terminal device 200a. As a result, the external computer is able to obtain information about images and articles of interest to the user P1 among the information displayed on the display unit 250 from the line of sight detection result, and the external computer may provide information appropriate to the user P1 based on the obtained information.

Figure 10:
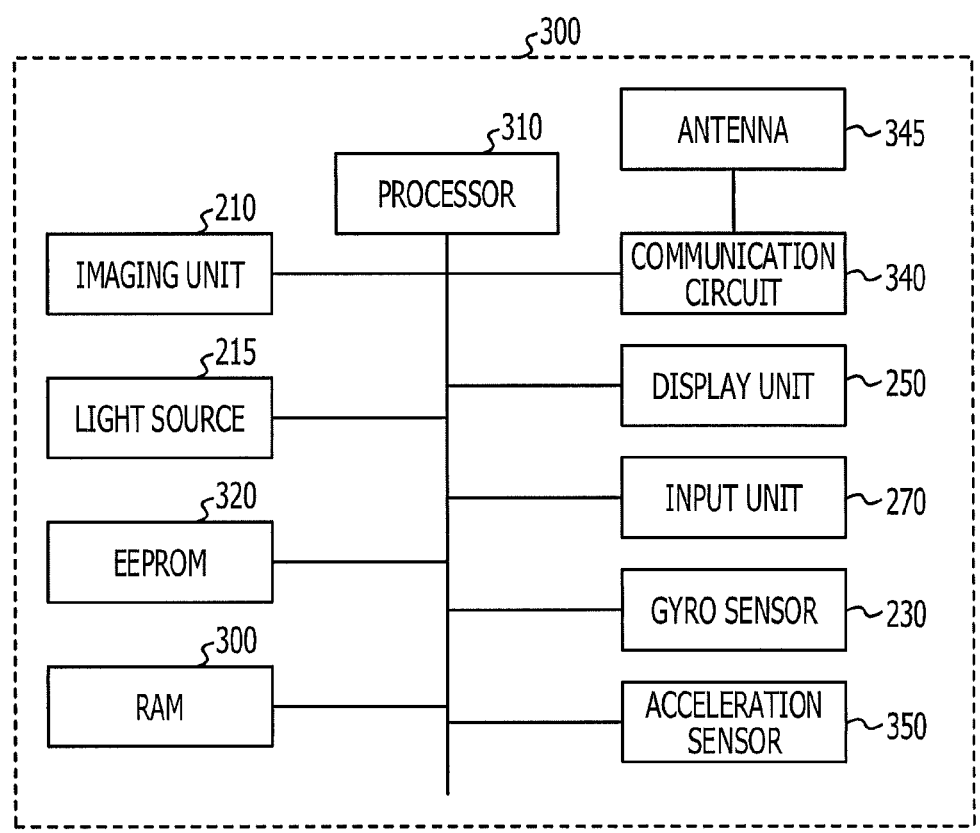
FIG. 10 describes an example of a hardware configuration of the terminal devices illustrated in FIG. 6 and in FIG. 8.

FIG. 10 describes an example of a hardware configuration of the terminal devices illustrated in FIG. 6 and in FIG. 8. Elements in a terminal device 300 illustrated in FIG. 10 that have the same or similar functions as the elements illustrated in FIG. 6 and FIG. 8 are provided with the same reference symbols and explanations thereof will be omitted.

The terminal device 300 includes the imaging unit 210, the light source 215, the gyro sensor 230, the display unit 250, the input unit 270, a processor 310, an EEPROM 320, a RAM 330, a communication circuit 340, an antenna 345, and an acceleration sensor 350. The imaging unit 210, the light source 215, the gyro sensor 230, the display unit 250, the input unit 270, the processor 310, the EEPROM 320, the RAM 330, the communication circuit 340, and the acceleration sensor 350 are interconnected through a bus. The communication circuit 340 and the antenna 345 are connected to each other.

The EEPROM 320, for example, stores an operating system of the terminal device 300. The EEPROM 320 stores an application program such as the line of sight detection program for the processor 310 to execute the line of sight detection processing illustrated in FIG. 7 and FIG. 9. If the terminal device 300 is an on-board device such as a car navigation device, the application program such as the line of sight detection program may be stored in a hard disk device and the like in place of the EEPROM 320.

The RAM 330 acts as the buffer unit 220, for example, and stores the images photographed and generated by the imaging unit 210.

The communication circuit 340 externally sends and receives data such as various application programs and electronic mail with wireless communication such as a wireless LAN or the Wi-Fi standard via the antenna 345.

The acceleration sensor 350 detects acceleration that indicates a movement of the terminal device 300 and outputs the detected acceleration as a portion of the information that indicates the state of the imaging unit 210 included in the terminal device 300. Specifically, both the acceleration sensor 350 and the gyro sensor 230 are examples of the obtaining unit that obtains the information that indicates the conditions during photographing by the imaging unit 210.

The application program such as the line of sight detection program may be distributed and stored, for example, on a removable disk such as an optical disk. The terminal device 300 may be, for example, connected to a network such as the Internet through the communication circuit 340 and the antenna 345 and may download the application program such as the line of sight detection program and store the application program in the EEPROM 320 and the like.

For example, the processor 310 realizes the determining unit 241 and 241a, the detecting unit 242, the specifying unit 243, and the obtaining unit 244 illustrated in FIG. 6 and FIG. 8 by executing the line of sight detection program stored in the EEPROM 320 and the like. Specifically, the processor 310 is an example of the detecting unit and the determining unit.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A terminal device comprising:
a processor; and
a memory which stores a plurality of instructions, which when executed by the processor, cause the processor to execute,
obtaining information that indicates each state of an imaging unit in each timing of photographing a subject;
determining whether each image photographed by the imaging unit includes blurriness based on the obtained information;
detecting a region including an eye in a first image and detecting a line of sight of the photographed subject in the detected region when the first image is determined as not including blurriness;
when a second image photographed after the first image is determined as including blurriness, detecting a region including an eye in the second image based on a first corresponding region in an image taken before the second image, the first corresponding region corresponding to the detected region in the first image; and
when a third image photographed after the first image is determined as not including blurriness, detecting a region including an eye in the third image based on a second corresponding region in an image taken before the third image and detecting a line of sight of the photographed subject in the detected region based on the detected region in the third image, the second corresponding region corresponding to the detected region in the first image.

2. The device according to claim 1,
wherein the obtaining involves obtaining information indicating a state of the terminal device as the information indicating the each state of the imaging unit; and
wherein the determining involves determining that the each image photographed by the imaging unit includes blurriness if a magnitude of a change of the indicated state in the information that indicates the state is equal to or greater than a certain value.

3. The device according to claim 1,
further comprising specifying the position of the subject in a third image based on the position of the subject in the first image when the third image photographed at a time after the first image is determined as not including blurriness.

4. A terminal device according to claim 1,
further comprising detecting a region including an eye in a first image without using the each image photographed before the first image.

5. A line of sight detection method comprising:
obtaining information that indicates each state of an imaging unit in each timing of photographing a subject;
determining, by a computer processor, whether each image photographed by the imaging unit includes blurriness based on the obtained information;
detecting a region including an eye in a first image and detecting a line of sight of the photographed subject in the detected region when the first image is determined as not including blurriness;
when a second image photographed after the first image is determined as including blurriness, detecting a region including an eye in the second image based on a first corresponding region in an image taken before the second image, the first corresponding region corresponding to the detected region in the first image; and when a third image photographed after the first image is determined as not including blurriness, detecting a region including an eye in the third image based on a second corresponding region in an image taken before the third image and detecting a line of sight of the photographed subject in the detected region based on the detected region in the third image, the second corresponding region corresponding to the detected region in the first image.

6. The method according to claim 5,
wherein the obtaining involves obtaining information indicating a state of the terminal device as the information indicating the each state of the imaging unit; and wherein the determining involves determining that the each image photographed by the imaging unit includes blurriness if a magnitude of a change of the indicated state in the information that indicates the state is equal to or greater than a certain value.

7. The method according to claim 5,
wherein the obtaining involves associating pixels included in a first image and a second image photographed before the first image among a plurality of images generated by the imaging unit continuously photographing the subject, and obtains a magnitude of an image region in which are dispersed pixels for which a difference between extracted feature quantities of the first image and extracted feature quantities of the second image is equal to or greater than a certain threshold, as the information indicating the each state of the imaging unit; and wherein the determining involves determining that the first image includes blurriness if the magnitude of the image region is equal to or greater than a certain value.

8. A non-transitory computer-readable storage medium storing a line of sight detection program that causes a computer to execute a process comprising:
obtaining information that indicates each state of an imaging unit in each timing of photographing a subject;
determining whether each image photographed by the imaging unit includes blurriness based on the obtained information;

detecting a region including an eye in a first image and detecting a line of sight of the photographed subject in the detected region when the first image is determined as not including blurriness;

when a second image photographed after the first image is determined as including blurriness, detecting a region including an eye in the second image based on a first corresponding region in an image taken before the second image, the first corresponding region corresponding to the detected region in the first image; and when a third image photographed after the first image is determined as not including blurriness, detecting a region including an eye in the third image based on a second corresponding region in an image taken before the third image and detecting a line of sight of the photographed subject in the detected region based on the detected region in the third image, the second corresponding region corresponding to the detected region in the first image.

9. The non-transitory computer-readable storage medium according to claim 8,
wherein the obtaining involves obtaining information indicating a state of the terminal device as the information indicating the each state of the imaging unit; and wherein the determining involves determining that the each image photographed by the imaging unit includes blurriness if a magnitude of a change of the indicated state in the information that indicates the state is equal to or greater than a certain value.

10. The non-transitory computer-readable storage medium according to claim 8,
wherein the obtaining involves associating pixels included in a first image and a second image photographed before the first image among a plurality of images generated by the imaging unit continuously photographing the subject, and obtains a magnitude of an image region in which are dispersed pixels for which a difference between extracted feature quantities of the first image and extracted feature quantities of the second image is equal to or greater than a certain threshold, as the information indicating the each state of the imaging unit; and wherein the determining involves determining that the first image includes blurriness if the magnitude of the image region is equal to or greater than a certain value.

\* \* \* \* \*